United States Patent
Foster et al.

(10) Patent No.: US 11,517,747 B2
(45) Date of Patent: Dec. 6, 2022

(54) HIS LEAD WITH EXTENSIBLE ELECTRODE AND REPOSITIONING FEATURES

(71) Applicant: Cardiac Pacemakers, Inc., St. Paul, MN (US)

(72) Inventors: Arthur J. Foster, Blaine, MN (US); Matthew J. Miller, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/601,119

(22) Filed: Oct. 14, 2019

(65) Prior Publication Data

US 2020/0114146 A1 Apr. 16, 2020

Related U.S. Application Data

(60) Provisional application No. 62/746,195, filed on Oct. 16, 2018.

(51) Int. Cl.
*A61N 1/05* (2006.01)
*A61N 1/375* (2006.01)
*A61N 1/362* (2006.01)

(52) U.S. Cl.
CPC .......... *A61N 1/0573* (2013.01); *A61N 1/362* (2013.01); *A61N 1/37512* (2017.08); *A61N 1/37518* (2017.08); *A61N 2001/058* (2013.01)

(58) Field of Classification Search
CPC .. A61N 1/057; A61N 1/0573; A61N 1/37518; A61N 1/0558; A61N 1/059; A61N 2001/0578
See application file for complete search history.

(56) References Cited

U.S. PATENT DOCUMENTS 4,214,804 A 7/1980 Little
4,886,074 A 12/1989 Bisping
(Continued)

OTHER PUBLICATIONS

International Search Report and Written Opinion issued in PCT/US2019/028302, dated Jul. 19, 2019, 12 pages.
(Continued)

*Primary Examiner* — Eric D. Bertram
(74) *Attorney, Agent, or Firm* — Nelson Mullins Riley & Scarborough LLP

(57) ABSTRACT

An electrode assembly for the positioning of an electrode of an implantable medical lead includes a housing and an electrode subassembly. The housing includes a proximal end for connecting to the lead and a distal end. The housing defines a housing lumen extending between the proximal end and the distal end. The housing lumen includes internal screw threads extending along at least a portion of the housing lumen. The electrode subassembly is disposed at least partially within the housing lumen. The electrode subassembly includes a needle electrode and a coupler. The needle electrode is disposed coaxially with the longitudinal axis of the housing lumen. The coupler is disposed at a proximal end of the needle electrode. The coupler includes external screw threads engaged with the internal screw threads of the housing lumen such that rotation of the coupler moves the needle electrode along the longitudinal axis of the housing lumen.

8 Claims, 6 Drawing Sheets

(56) References Cited

U.S. PATENT DOCUMENTS

| | | | |
|---|---|---|---|
| 5,095,916 A | 3/1992 | Smits | |
| 5,353,800 A * | 10/1994 | Pohndorf | A61B 5/0215 600/486 |
| 5,492,119 A | 2/1996 | Abrams | |
| 6,704,605 B2 | 3/2004 | Soltis et al. | |
| 7,177,704 B2 | 2/2007 | Laske et al. | |
| 7,212,870 B1 | 5/2007 | Helland | |
| 7,212,871 B1 | 5/2007 | Morgan | |
| 7,319,905 B1 | 1/2008 | Morgan et al. | |
| 7,369,901 B1 | 5/2008 | Morgan et al. | |
| 7,418,298 B2 | 8/2008 | Shiroff et al. | |
| 7,433,739 B1 | 10/2008 | Salys et al. | |
| 7,496,410 B2 | 2/2009 | Heil, Jr. | |
| 7,546,166 B2 | 6/2009 | Michels et al. | |
| 7,657,326 B2 | 2/2010 | Bodner et al. | |
| 7,711,437 B1 | 5/2010 | Bornzin et al. | |
| 7,751,905 B2 | 7/2010 | Feldmann et al. | |
| 7,860,581 B2 | 12/2010 | Eckerdal et al. | |
| 7,920,927 B2 | 4/2011 | Zarembo et al. | |
| 7,920,928 B1 | 4/2011 | Fang et al. | |
| 8,000,805 B2 | 8/2011 | Swoyer et al. | |
| 8,036,756 B2 | 10/2011 | Swoyer et al. | |
| 8,036,757 B2 | 10/2011 | Worley | |
| 8,090,451 B2 | 1/2012 | Tyson, Jr. | |
| 8,346,374 B2 | 1/2013 | Foster et al. | |
| 8,406,899 B2 | 3/2013 | Reddy et al. | |
| 9,008,768 B2 | 4/2015 | Zhu et al. | |
| 9,302,098 B2 | 4/2016 | Zhang et al. | |
| 9,545,513 B2 | 1/2017 | Hastings et al. | |
| 9,579,501 B2 | 2/2017 | Shuros et al. | |
| 2003/0204233 A1 | 10/2003 | Laske et al. | |
| 2004/0054388 A1 | 3/2004 | Osypka | |
| 2004/0215307 A1 | 10/2004 | Michels et al. | |
| 2005/0113900 A1 | 5/2005 | Shiroff et al. | |
| 2006/0106315 A1 | 5/2006 | Edens | |
| 2006/0129218 A1 | 6/2006 | Swoyer et al. | |
| 2006/0155353 A1 | 7/2006 | Heil, Jr. | |
| 2007/0050003 A1 | 3/2007 | Zarembo et al. | |
| 2007/0050004 A1 | 3/2007 | Swoyer et al. | |
| 2007/0106202 A1 | 5/2007 | Salo et al. | |
| 2007/0129782 A1 | 6/2007 | Feldmann et al. | |
| 2007/0239241 A1 | 10/2007 | Tyson | |
| 2008/0065185 A1 | 3/2008 | Worley | |
| 2008/0109042 A1 | 5/2008 | Bodner et al. | |
| 2008/0249596 A1 | 10/2008 | Shiroff et al. | |
| 2008/0262588 A1 | 10/2008 | Zarembo et al. | |
| 2008/0288040 A1 | 11/2008 | Eckerdal et al. | |
| 2009/0259272 A1 | 10/2009 | Reddy et al. | |
| 2010/0305670 A1 | 12/2010 | Hall et al. | |
| 2010/0324644 A1 | 12/2010 | Levi et al. | |
| 2011/0009939 A1 | 1/2011 | Foster et al. | |
| 2011/0160817 A1 | 6/2011 | Foster et al. | |
| 2011/0199173 A1 | 8/2011 | Leijssen et al. | |
| 2011/0251662 A1 | 10/2011 | Griswold et al. | |
| 2012/0004714 A1 * | 1/2012 | Kleve | A61N 1/0573 607/116 |
| 2012/0179221 A1 | 7/2012 | Reddy et al. | |
| 2013/0261689 A1 | 10/2013 | Zhu et al. | |
| 2013/0296852 A1 * | 11/2013 | Madjarov | A61B 18/148 606/41 |
| 2014/0067036 A1 | 3/2014 | Shuros et al. | |
| 2014/0107755 A1 | 4/2014 | Jean-Francois | |
| 2014/0207149 A1 | 7/2014 | Hastings et al. | |
| 2014/0243946 A1 | 8/2014 | Zhang et al. | |
| 2015/0080995 A1 | 3/2015 | Seeley et al. | |
| 2015/0105729 A1 | 4/2015 | Valeti et al. | |
| 2015/0313669 A1 | 11/2015 | Darmos et al. | |
| 2017/0106185 A1 | 4/2017 | Orts et al. | |
| 2019/0022379 A1 * | 1/2019 | Foster | A61N 1/0573 |
| 2019/0321625 A1 * | 10/2019 | Shuros | A61N 1/0573 |

OTHER PUBLICATIONS

Search Report and Written Opinion issued in NL Application 2019577, dated Mar. 1, 2018, 7 pages.

International Search Report and Written Opinion issued in PCT/US2019/056095, dated Jan. 28, 2020, 14 pages.

* cited by examiner

HIS LEAD WITH EXTENSIBLE ELECTRODE AND REPOSITIONING FEATURES

CROSS-REFERENCE TO RELATED APPLICATION

This application claims priority to Provisional Application No. 62/746,195, filed Oct. 16, 2018, which is herein incorporated by reference in its entirety.

TECHNICAL FIELD

The present disclosure relates to medical devices and methods for the active fixation of an implantable medical lead. More specifically, the disclosure relates to devices and methods for active fixation of implantable medical leads for mapping and stimulating the bundle of His in a patient's heart.

BACKGROUND

Cardiac rhythm management systems are useful for electrically stimulating a patient's heart to treat various cardiac arrhythmias. A method of electrically stimulating the heart can include stimulating the His bundle at a location distal to the tricuspid valve at the interatrial septum in the right atrium of the heart or at a location proximate to the tricuspid valve at the interventricular septum in the right ventricle of the heart. Directly stimulating the bundle of His can simultaneously pace both the right and left ventricles of the heart, potentially avoiding pacing induced dyssynchrony which may occur with right ventricular apex pacing. There is a continuing need for improved His bundle lead designs and assemblies.

SUMMARY

Example 1 is an electrode assembly for the positioning of an electrode of an implantable medical lead. The electrode assembly includes a housing and an electrode subassembly. The housing includes a proximal end for connecting to the lead and a distal end opposite the proximal end. The housing defines a housing lumen having a longitudinal axis. The housing lumen extends between the proximal end and the distal end. The housing lumen includes internal screw threads extending along at least a portion of the housing lumen. The electrode subassembly is disposed at least partially within the housing lumen. The electrode subassembly includes a needle electrode and a coupler. The needle electrode is disposed coaxially with the longitudinal axis of the housing lumen. The coupler is disposed at a proximal end of the needle electrode. The coupler includes external screw threads engaged with the internal screw threads of the housing lumen such that rotation of the coupler moves the needle electrode along the longitudinal axis of the housing lumen.

Example 2 is the electrode assembly of Example 1, wherein rotation of the coupler in a first direction moves the coupler and the needle electrode toward the distal end of the housing, and rotation of the coupler in a second direction opposite the first direction moves the coupler and the needle electrode toward the proximal end of the housing.

Example 3 is the electrode assembly of either of Examples 1 or 2, further including an active fixation device connected to the housing.

Example 4 is the electrode assembly of Example 3, wherein the active fixation device includes a plurality of tines connected to the housing and projecting from the distal end of the housing, the tines self-biasing from a linear configuration to a curved configuration.

Example 5 is the electrode assembly of Example 3, wherein the active fixation device includes a fixation helix connected to the housing and projecting from the distal end of the housing.

Example 6 is the electrode assembly of any of Examples 3-5, wherein when the coupler is disposed at a distal end of the portion of the housing lumen including the internal screw threads, a distal end of the needle electrode projects from the distal end of the housing and distally beyond the active fixation device.

Example 7 is the electrode assembly of any of Examples 1-6, wherein the needle electrode includes a conical tip.

Example 8 is the electrode assembly of any of Examples 1-7, wherein the housing is formed of an insulative material.

Example 9 is the electrode assembly of any of Examples 1-8, wherein the coupler is rotatable by a stylet.

Example 10 is the electrode assembly of any of Examples 1-9, wherein the coupler is rotatable by a coil conductor.

Example 11 is an implantable medical lead including a tubular lead body, a connector assembly, a first electrical conductor, and an electrode assembly. The lead body is flexible and includes a proximal end and a distal end. The connector assembly is disposed at the proximal end of the lead body. The first electrical conductor extends from the connector assembly to the distal end of the lead body. The electrode assembly is according to any of Examples 1-8. The electrode assembly is disposed at the distal end of the lead body. The first electrical conductor is electrically connected to the needle electrode.

Example 12 is the lead of Example 11, wherein the coupler is rotatable by a stylet extending from the proximal end of the lead body to the coupler.

Example 13 is the lead of Example 11, wherein the first electrical conductor is a coil conductor, the connector assembly includes a terminal pin connected to a distal end of the coil conductor, and the coil conductor is mechanically connected to the coupler such that rotation of the terminal pin rotates the coupler.

Example 14 is the lead of any of Examples 11-14, wherein the electrode assembly is according to any of Examples 3-8, the lead further including a second electrical conductor extending from the connector assembly to the distal end of the lead body, the second electrical conductor electrically connected to the active fixation device.

Example 15 is a method of making an electrode assembly for the positioning of an electrode of an implantable medical lead. The method includes attaching an active fixation device to a housing such that the active fixation device extends beyond a distal end of the housing, attaching a coupler including external screw threads to a proximal end of a needle electrode, inserting a distal end of the needle electrode into a housing lumen at a proximal end of the housing, the housing lumen extending from the proximal end of the housing to the distal end of the housing, inserting the coupler into the housing lumen at the proximal end of the housing, and engaging the external screw threads of the coupler with internal threads extending along at least a portion of the housing lumen.

Example 16 is an electrode assembly for the positioning of an electrode of an implantable medical lead. The electrode assembly includes a housing and an electrode subassembly. The housing includes a proximal end for connecting to the lead and a distal end opposite the proximal end. The housing defines a housing lumen having a longitudinal axis.

The housing lumen extends between the proximal end and the distal end. The housing lumen includes internal screw threads extending along at least a portion of the housing lumen. The electrode subassembly is disposed at least partially within the housing lumen. The electrode subassembly includes a needle electrode and a coupler. The needle electrode is disposed coaxially with the longitudinal axis of the housing lumen. The coupler is disposed at a proximal end of the needle electrode. The coupler includes external screw threads engaged with the internal screw threads of the housing lumen such that rotation of the coupler in a first direction moves the coupler and the needle electrode along the longitudinal axis of the housing lumen toward the distal end of the housing, and rotation of the coupler in a second direction opposite the first direction moves the coupler and the needle electrode along the longitudinal axis of the housing lumen toward the proximal end of the housing.

Example 17 is the electrode assembly of Example 16, further including an active fixation device connected to the housing.

Example 18 is the electrode assembly of Example 17, wherein when the coupler is disposed at a distal end of the portion of the housing lumen including the internal screw threads, a distal end of the needle electrode projects from the distal end of the housing and distally beyond the active fixation device.

Example 19 is the electrode assembly of either of Examples 17 or 18, wherein the active fixation device includes a plurality of tines connected to the housing and projecting from the distal end of the housing, the tines self-biasing from a linear configuration to a curved configuration.

Example 20 is the electrode assembly of either of Examples 17 or 18, wherein the active fixation device includes a fixation helix connected to the housing and projecting from the distal end of the housing.

Example 21 is the electrode assembly of any of Examples 16-20, wherein the needle electrode includes a conical tip.

Example 22 is the electrode assembly of any of Examples 16-21, wherein the housing is formed of an insulative material.

Example 23 is the electrode assembly of any of Examples 16-22, wherein the coupler is rotatable by a stylet.

Example 24 is the electrode assembly of any of Examples 16-22, wherein the coupler is rotatable by a coil conductor.

Example 25 is an implantable medical lead including a tubular lead body, a connector assembly, a first electrical conductor, and an electrode assembly. The lead body is flexible and includes a proximal end and a distal end. The connector assembly is disposed at the proximal end of the lead body. The first electrical conductor extends from the connector assembly to the distal end of the lead body. The electrode assembly includes a housing and an electrode subassembly. The housing includes a proximal end for connecting to the lead and a distal end opposite the proximal end. The housing defines a housing lumen having a longitudinal axis. The housing lumen extends between the proximal end and the distal end. The housing lumen includes internal screw threads extending along at least a portion of the housing lumen. The electrode subassembly is disposed at least partially within the housing lumen. The electrode subassembly includes a needle electrode and a coupler. The needle electrode is disposed coaxially with the longitudinal axis of the housing lumen. The first electrical conductor is electrically connected to the needle electrode. The coupler is disposed at a proximal end of the needle electrode. The coupler includes external screw threads engaged with the internal screw threads of the housing lumen such that rotation of the coupler moves the needle electrode along the longitudinal axis of the housing lumen.

Example 26 is the lead of Example 25, wherein the coupler is rotatable by a stylet extending from the proximal end of the lead body to the coupler.

Example 27 is the lead of either of Examples 25 or 26, wherein the first electrical conductor is a coil conductor, the connector assembly includes a terminal pin connected to a distal end of the coil conductor, and the coil conductor is mechanically connected to the coupler such that rotation of the terminal pin rotates the coupler.

Example 28 is the lead of any of Examples 25-27, further including an active fixation device connected to the housing.

Example 29 is the lead of Example 28, wherein when the coupler is disposed at a distal end of the portion of the housing lumen including the internal screw threads, a distal end of the needle electrode projects from the distal end of the housing and distally beyond the active fixation device.

Example 30 is the lead of either of Examples 28 or 29, wherein the active fixation device includes a plurality of tines connected to the housing and projecting from the distal end of the housing, the tines self-biasing from a linear configuration to a curved configuration.

Example 31 is the lead of either of Examples 28 or 29, wherein the active fixation device includes a fixation helix connected to the housing and projecting from the distal end of the housing.

Example 32 is the lead of any of Examples 25-31, further including a second electrical conductor extending from the connector assembly to the distal end of the lead body, the second electrical conductor electrically connected to the active fixation device.

Example 33 is the lead of any of Examples 25-32, wherein the needle electrode includes a conical tip.

Example 34 is the lead of any of Examples 25-33, wherein the housing is formed of an insulative material.

Example 35 is a method of making an electrode assembly for the positioning of an electrode of an implantable medical lead. The method includes attaching an active fixation device to a housing such that the active fixation device extends beyond a distal end of the housing, attaching a coupler including external screw threads to a proximal end of a needle electrode, inserting a distal end of the needle electrode into a housing lumen at a proximal end of the housing, the housing lumen extending from the proximal end of the housing to the distal end of the housing, inserting the coupler into the housing lumen at the proximal end of the housing, and engaging the external screw threads of the coupler with internal threads extending along at least a portion of the housing lumen.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
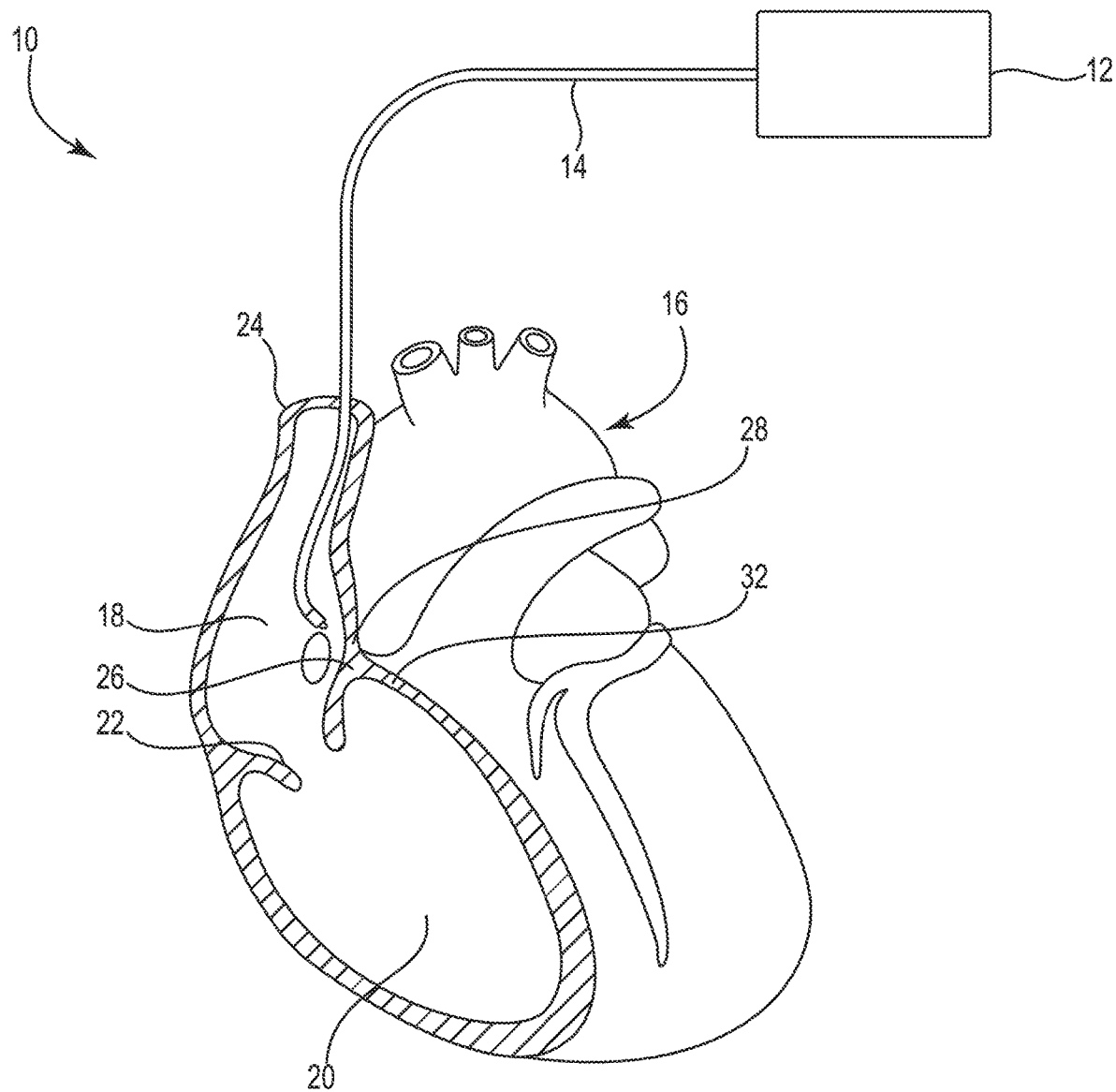
FIG. 1 is a schematic view of system for mapping and stimulating the bundle of His in a patient's heart, including a lead according to some embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of system 10 for mapping and stimulating the bundle of His, according to embodiments of this disclosure. As shown in FIG. 1, the system 10 includes an implantable pulse generator 12 coupled to a lead 14 deployed in a patient's heart 16. The pulse generator 12 generates an electrical pacing stimulus to be delivered to the heart 16. The lead 14 operates to convey electrical signals and stimuli between the heart 16 and the pulse generator 12. As further shown in FIG. 1, the heart 16 includes a right atrium 18 and a right ventricle 20 separated by a tricuspid valve 22. In the embodiment shown in FIG. 1, the lead 14 enters the vascular system through a vascular entry site (not shown) and a superior vena cava 24 to be implanted in the right atrium 18. The bundle of His 26 can be stimulated at an atrial location proximate to the tricuspid valve 22 at an interatrial septum 28 in the right atrium 18, as shown in FIG. 1. This location is proximate to the apex of the triangle of Koch. Alternatively, the bundle of His 26 can be stimulated at a ventricular location distal to the tricuspid valve 22 at an interventricular septum 32 in the right ventricle 20 by passing the lead 14 through the tricuspid valve 22 and into the right ventricle 20.

The system 10 allows direct therapeutic stimulation of the bundle of His 26 by fixating the lead 14 at one of the locations describe above. Mapping at one of the locations described above is necessary to be able to position the lead 14 close enough to the bundle of His 26 for efficient and effective pacing. Some prior art leads rely on non-contact sensing or surface contact sensing with electrodes to map the location of the bundle of His 26. However, in some instances, this may not be accurate enough to identify the proper location to implant the lead 14. Such precise mapping can require repeated penetration of the myocardium to achieve the sensitivity necessary to accurately locate the bundle of His 26. In some other prior art leads, a helical electrode can be employed to repeatedly penetrate the myocardium to locate the bundle of His 26. However, repeatedly implanting and removing the helical electrode, which requires multiple rotations of the helical electrode, can be time consuming and may damage the myocardium. In addition, once a suitable location is found, the recoil from the force required to implant the helical electrode to fixate the prior art lead can result in the helical electrode moving from the identified location and being implanted in a less suitable location. Embodiments of the present disclosure permit mapping that is faster and less harmful to the myocardium, while providing for fixation of the lead 14 that accurately secures a lead electrode in the myocardium at the bundle of His 26.

Although the description above is with respect to His bundle pacing, it is understood that embodiments may be employed for conduction system pacing generally, such as for left bundle branch pacing, for example. Thus, using embodiments of the present disclosure, the His/Purkinje system may be directly paced at either location of the bundle of His or at the left branch bundle at the intraventricular septum area.

Figure 2:
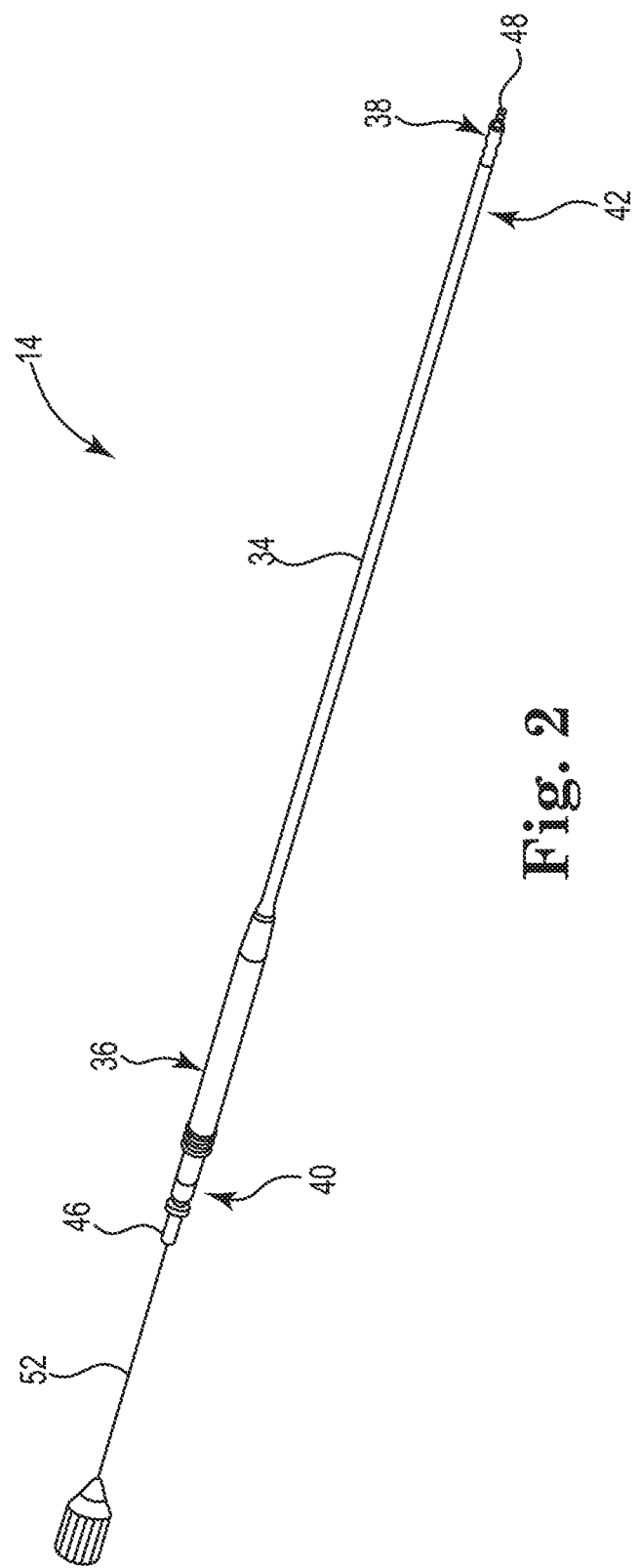
FIG. 2 is a perspective view of the lead of FIG. 1, according to some embodiments of this disclosure.
Figure 3:
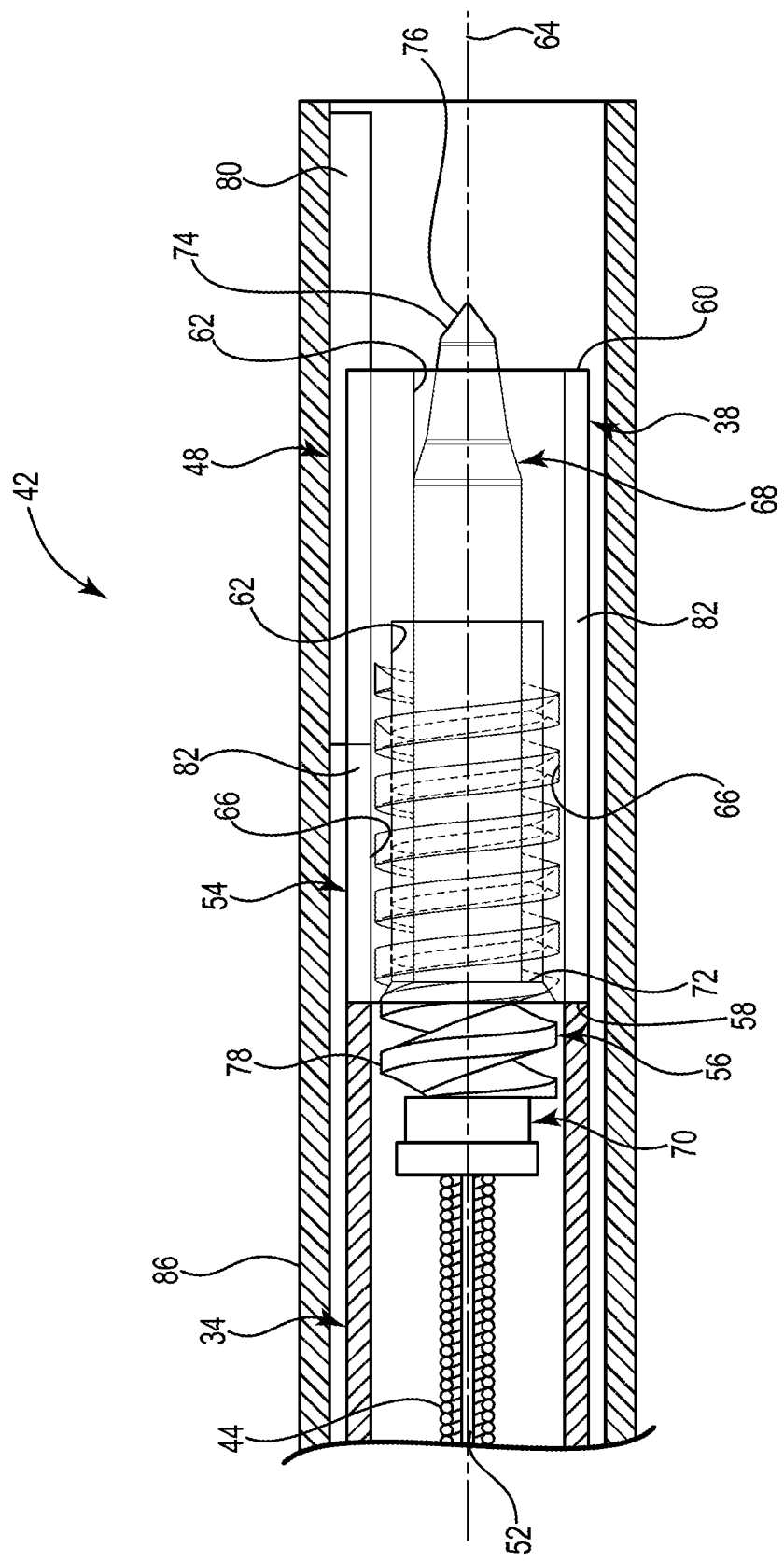
FIG. 3 is schematic partial cross-sectional side view of a distal end of the lead of FIG. 2 showing a device for the positioning of an electrode in an undeployed configuration, according to some embodiments of this disclosure.

FIG. 2 is a perspective view of the lead 14 of FIG. 1, according to embodiments of this disclosure. As shown in FIG. 2, the lead 14 includes a lead body 34, a connector assembly 36, and an electrode assembly 38. The lead body 34 is a flexible tubular body including a proximal end 40 and a distal end 42, and containing a first electrical conductor 44 (FIG. 3) extending from the proximal end 40 to the distal end 42. The connector assembly 36 is disposed at the proximal end 40 and includes a terminal pin 46 electrically connected to the first electrical conductor 44. The connector assembly 36 is configured to electrically couple the lead 14 to the pulse generator 12 (FIG. 1). The electrode assembly 38 is disposed at the distal end 42 of the lead 14 and can include an active fixation device 48. The electrode assembly 38 is a device for the positioning of a needle electrode 50 (FIG. 3). In the embodiment of FIG. 2, the first electrical conductor 44 is electrically connected to the needle electrode 50 so that it can function as an active electrode to stimulate the bundle of His 26 (FIG. 1).

In some embodiments, a stylet 52 can be extended through connector assembly 36 and the lead body 34 to the electrode assembly 38 and engage the electrode assembly 38 such that rotation of the stylet 52 deploys the needle electrode 50, as described below.

FIG. 3 is schematic partial cross-sectional side view of the distal end 42 of the lead 14 of FIG. 2 showing the electrode assembly 38 according to some embodiments of this disclosure. As shown in FIG. 3, the electrode assembly 38 can include a housing 54 and an electrode subassembly 56. The housing 54 can include a proximal end 58 and a distal end 60 opposite the proximal end 58. The housing 54 can define a housing lumen 62 having a longitudinal axis 64. The housing lumen 62 can extend between the proximal end 58 and the distal end 60. The housing lumen 62 can include internal screw threads 66 extending along at least a portion of the housing lumen 62.

The electrode subassembly 56 can include a needle electrode 68 and a coupler 70. The needle electrode 68 can include a proximal end 72, a distal end 74 opposite the proximal end 72, and a conical tip 76 at the distal end 74. The coupler 70 can include external screw threads 78. The coupler 70 may be disposed at the proximal end 72 of the needle electrode 68. The coupler 70 may be mechanically connected to the needle electrode 68 by an adhesive, a threaded connection, and/or by molding or extruding the coupler 70 around the proximal end 72, for example.

In some embodiments, the housing 54 may be formed of an electrically insulative material or a conductive material coated with an insulative material. Insulative materials may include a polymeric material or a ceramic material. Polymeric materials may include polyetheretherketone, epoxy, polyurethane, or parylene, for example. Ceramic materials may be deposited, fired, molded, and/or machined. In some other embodiments, the housing 54 may be formed of an electrically conductive material provided that the coupler 70 is formed of an electrically non-conducting material, as described below.

In some embodiments, the needle electrode 68 includes an electrically conductive material. In some embodiments, the needle electrode 68 consists essentially of a conductive material. In some embodiments, the needle electrode 68 consists of a conductive material. In some embodiments, the needle electrode 68 may include MP35N, Elgiloy, MP35N LT, platinum alloys, stainless steel alloys, palladium alloys, and titanium. In some embodiments, the needle electrode 68 may include any of the foregoing conductive material plated or deposited by powdered metallurgy over a ceramic material or a polymer material. In some embodiments, the needle electrode 68 may include a conductive material that is radiopaque, such as tungsten, platinum alloys, palladium alloys or iridium alloys, for example.

In some embodiments, the coupler 70 may be formed of an electrically non-conducting material, such as, polyetheretherketone, epoxy, polyurethane or ceramic, for example. In such embodiments, the coupler 70 may define a pathway (not shown) through the coupler 70 to the needle electrode 68 to permit the first electrical conductor 44 to electrically connect to the needle electrode 68 by welding, soldering, or a conductive adhesive, for example. Alternatively, or additionally, the coupler 70 may itself include a conductive pathway (not shown) connecting the first electrical conductor 44 to the needle electrode 68. In other embodiments, the coupler 70 may be formed of an electrically conductive material, such as MP35N, Elgiloy, MP35N LT, platinum alloys, stainless steel alloys, palladium alloys, and titanium, for example. In such embodiments, the first electrical conductor 44 may be electrically connected to the needle electrode 68 by the coupler 70 itself.

In some embodiments, the first electrical conductor 44 may be a coil conductor, as shown in FIG. 3. In some other embodiments, the first electrical conductor 44 may be a straight wire conductor.

As shown in FIG. 3, the needle electrode 68 can be disposed coaxially with the longitudinal axis 64 of the housing lumen 62. The external screw threads 78 of the coupler 70 can engage with the internal screw threads 66 of the housing lumen 62. In the embodiment shown in FIG. 3, the coupler 70 is rotatable by the stylet 52 which can engage a slot (not shown) in the coupler 70 to engage a flat-bladed stylet. The stylet 52 and corresponding engagement structure in the coupler 70 can be other shapes, such as a cross-recess, a hexagonal recess, or a star recess. In some other embodiments in which the first electrical conductor 44 is a coil conductor, the coupler 70 may be rotatable by the coil conductor.

The electrode assembly 38 can further include the active fixation device 48 connected to the housing 54. In the embodiment of FIG. 3, the active fixation device 48 can include a plurality of tines 80. In some embodiments, each of the tines 80 can be disposed in a longitudinal groove 82 at an outer surface of the housing 54. Each of tines 80 may be attached to housing 54 by an adhesive, for example. In some other embodiments, the tines 80 may be molded into the housing 54.

In some embodiments, the active fixation device 48 includes at least three tines 80. In some embodiments, the active fixation device 48 consists of three tines 80. In some other embodiments, the active fixation device 48 consists of four tines 80. The embodiment of FIG. 3 includes four tines 80, one shown in FIG. 3 with the remaining three omitted for clarity. The tine 80 is formed of a material having a shape memory, for example nitinol or a gold/stainless steel alloy, such that the tine 80 can self-biased to be curved configuration when unrestrained (FIG. 5) and can be in a linear configuration when restrained by a placement catheter 86, as shown in FIG. 3. The tine 80 may be pointed (not shown) for ease in entering tissue for fixation.

For clarity of illustration, in FIGS. 3-6, the housing 54 is shown in phantom view, while the lead body 34, the first electrical connector 44, and the placement catheter 86 are shown in cross-section, and the stylet 52, needle electrode 68, coupler 70, and tine 80 are shown in side view.

In use, rotating the coupler 70 in a first direction moves the coupler 70 toward the distal end 60, moving the needle electrode 68 toward the distal end 60 of the housing 54 and out of the housing lumen 62 to project from the distal end 60. Rotating the coupler 70 in a second direction opposite the first direction moves the coupler 70 and the needle electrode 68 toward the proximal end 58 of the housing 54, retracting the needle electrode 68 at least partially into the housing lumen 62. In the embodiment of FIG. 3, rotation of the coupler 70 is driven by rotating the stylet 52. In other embodiments, rotation of the coupler 70 may be driven by rotating the terminal pin 46, which rotates a coil conductor, such as the first electrical conductor 44.

Figure 4:
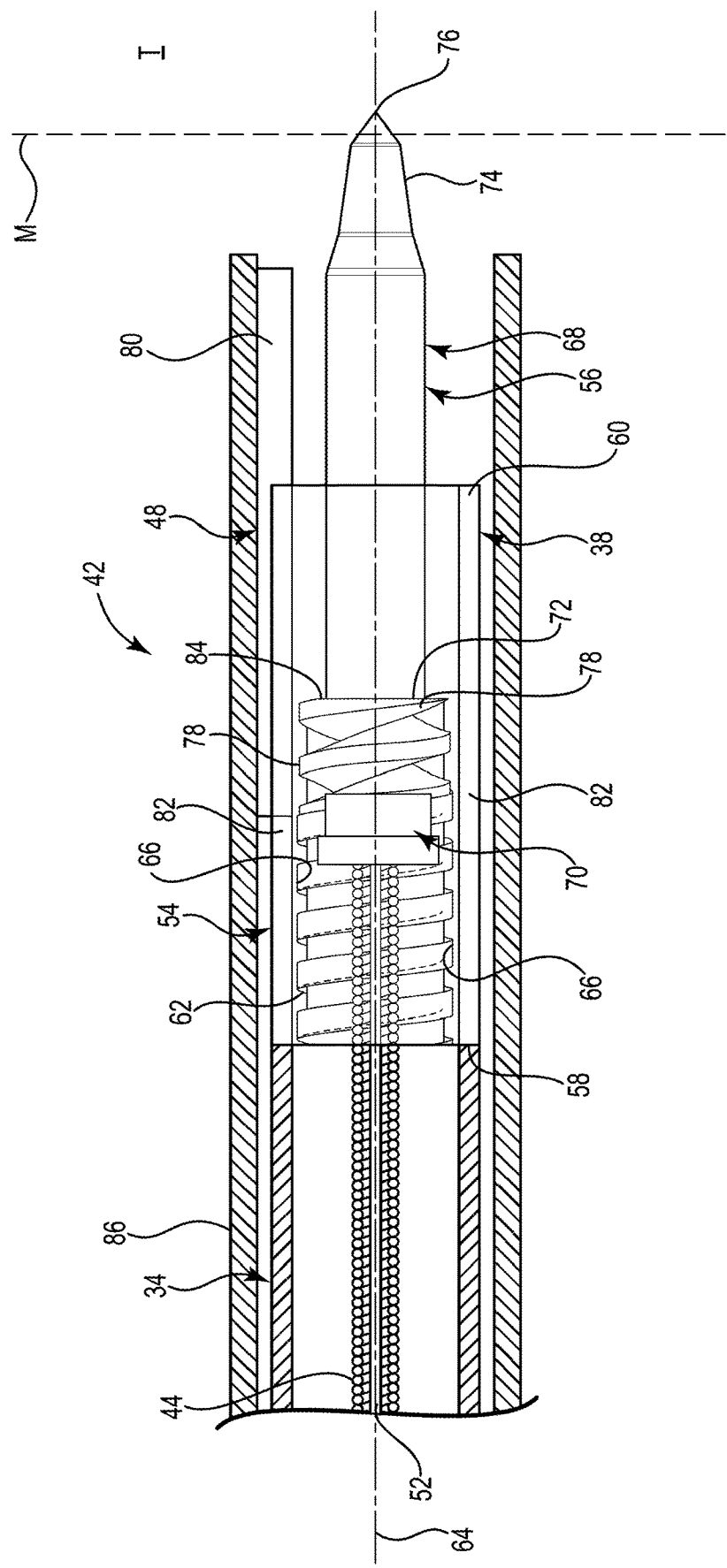
FIG. 4 is schematic partial cross-sectional side view of the distal end of the lead of FIG. 3 showing the device in a mapping configuration, according to some embodiments of this disclosure.

FIG. 4 is schematic partial cross-sectional side view of the distal end 42 of the lead 14 of FIG. 3 showing the electrode assembly 38 in a mapping configuration, according to some embodiments of this disclosure. In FIG. 4, the coupler 70 has been rotated in the first direction until it is disposed at a distal end 84 of the portion of the housing lumen 62 including the internal screw threads 66. In this configuration, the distal end 74 of the needle electrode 68 projects from the distal end 60 of the housing 54 and distally beyond the active fixation device 48. Thus, in the embodiment of FIG. 4, the distal end 74 of the needle electrode 68 projects beyond the tines 80.

In operation, the system 10 with the lead 14 having the electrode assembly 38 as described above, can be used as shown in FIG. 4 to map one of the locations described above in reference to FIG. 1 for accessing the bundle of His 26. The needle electrode 68 can penetrate into the myocardium M at a first spot near the bundle of His 26, measurements made, the needle electrode 68 quickly removed from the myocardium M and moved to a second spot where the process is repeated. The actions of penetrating the myocardium M with the needle electrode 68 by simply pushing on the lead 14 and removing the needle electrode 68 from the myocardium M by simply pulling on the lead 14 are faster and may cause less tissue damage than the prior art which required many turns of a helical electrode to either penetrate the myocardium M or remove the electrode. Thus, embodiments of the disclosure can provide rapid and accurate mapping before positioning of the lead 14 close enough to the bundle of His 26 for efficient and effective pacing.

Figure 5:
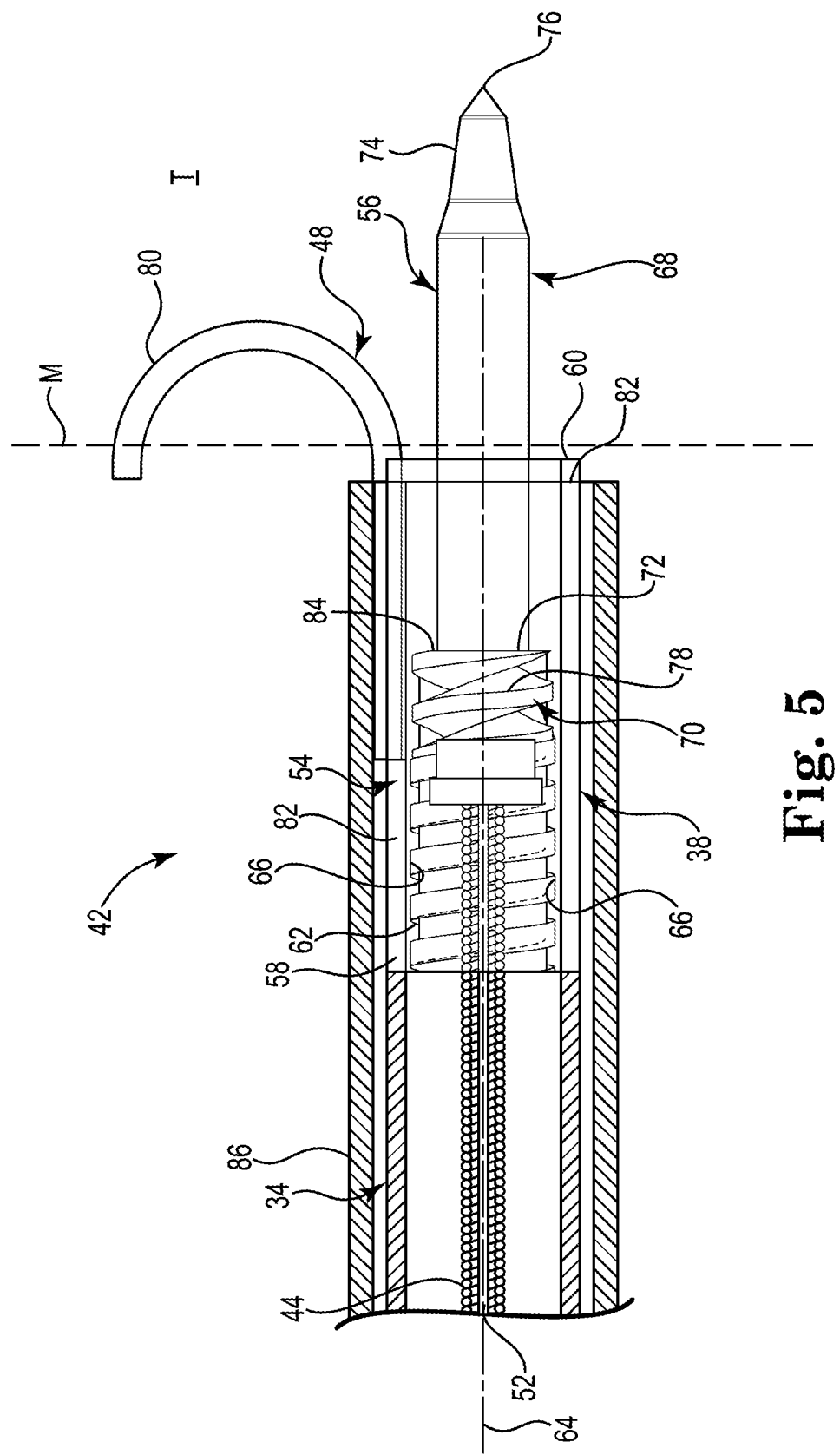
FIG. 5 is schematic partial cross-sectional side view of the distal end of the lead of FIG. 4 showing the device in a deployed configuration, according to some embodiments of this disclosure.

FIG. 5 is schematic partial cross-sectional side view of the distal end 42 of the lead 14 of FIG. 4 showing the electrode assembly 38 with the active fixation device 48 deployed, according to some embodiments of this disclosure. Once a suitable pacing location is found and the conical tip 76 of the needle electrode 68 has penetrated the myocardium M, the active fixation device 48 can be deployed to fixate the lead 14.

The active fixation device 48 can be deployed by drawing back the placement catheter 86 as pressure is applied to the lead 14 in the distal direction to drive the tines 80 through the myocardium M and into the tissue T and to drive the tip 76 further into the tissue T. As they are released from the restraint of the placement catheter 86, the tines 80 self-bias from a linear configuration to a curved configuration, penetrating through the tissue T in the curved configuration, thus implanting the active fixation device 48 and fixating the lead 14. In some embodiments, the tines 80 curve back out through the myocardium M. Advantageously, the needle electrode 68 is less likely to move from the desired pacing location due to recoil from the force required to implant the active fixation device 48 because the needle electrode 68 has penetrated the myocardium M and into the tissue T.

Once the lead 14 is fixated, the coupler 70 may be rotated in the second direction to move the distal end 74 of the needle electrode 68 proximally through the tissue T and back toward the myocardium M and/or rotated in the first direction to move the distal end of 74 distally into the tissue T. In this way, a penetration depth of the needle electrode 68 can be adjusted to find the best depth for stimulation of the bundle of His 26 (FIG. 1).

Figure 6:
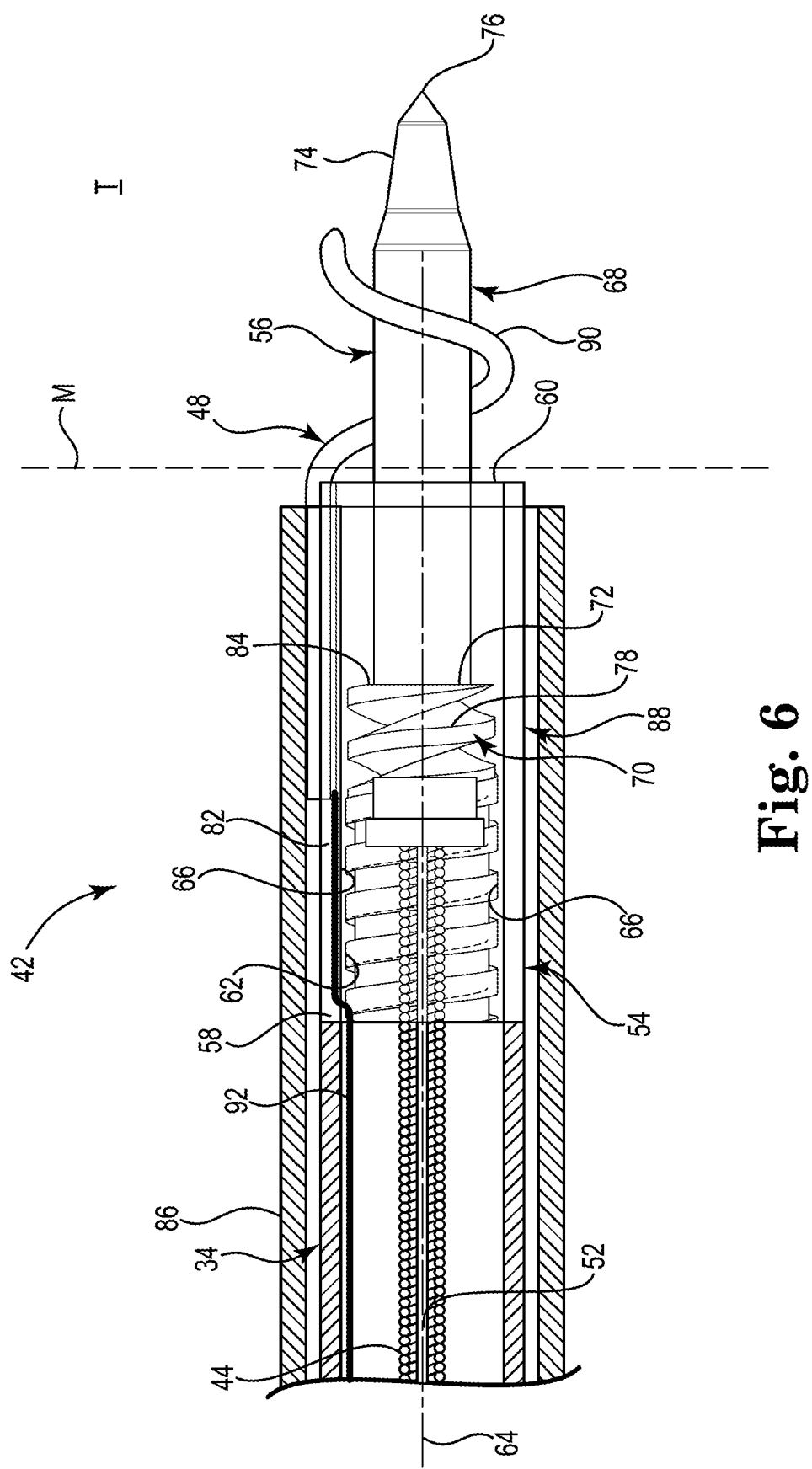
FIG. 6 is schematic partial cross-sectional side view of the distal end of the lead of FIG. 2 showing another device for the positioning of an electrode in a deployed configuration, according to some embodiments of this disclosure.

FIG. 6 is schematic partial cross-sectional side view of the distal end 42 of the lead 14 of FIG. 2 showing another electrode assembly 88 for the positioning of an electrode in a deployed configuration, according to some embodiments of this disclosure. The embodiment of FIG. 6 is identical to the embodiment of FIGS. 3-5, except that the active fixation device 48 includes a fixation helix 90 instead of the plurality of tines 80, and the lead 14 further includes a second electrical conductor 92 extending from the connector assembly 36 to the distal end 42 of the lead 14. The second electrical conductor 92 can be electrically connected to the fixation helix 90 of the active fixation device 48 so that, once deployed, the fixation helix 90 can also function as a close-set anode or a redundant cathode for stimulating the bundle of His 26 (FIG. 1).

The fixation helix 90 may be formed of a conductive material, such as MP35N, Elgiloy, MP35N LT, platinum alloys, stainless steel alloys, palladium alloys, and titanium, for example. The active fixation device 48 can be deployed by applying pressure to the lead 14 in the distal direction while also rotating the lead 14 to screw the fixation helix 90 through the myocardium M and into the tissue T, thus implanting the active fixation device 48 and fixating the lead 14. As with the embodiment described above in reference to FIG. 5, the needle electrode 68 is less likely to move from the desired pacing location due to recoil from the force required to implant the active fixation device 48 because the needle electrode 68 has penetrated the myocardium M and into the tissue T.

The electrode assembly 38 or electrode assembly 88, can be made by attaching the active fixation device 48 to the housing 54 such that the active fixation device 48 extends beyond the distal end 60 of the housing 54. In some embodiments, the active fixation device 48 may be attached in the longitudinal grooves 82. The coupler 70 can be attached to the proximal end 72 of the needle electrode 68. The distal end 74 of the needle electrode 68 can be inserted into the housing lumen 62 at the proximal end 58 of the housing 54. The external screw threads 78 of the coupler 70 can engage with the internal screw threads 66.

Although the embodiment of FIG. 6 is shown with the second electrical conductor 90 electrically connected to the active fixation device, it is understood that the embodiment of FIGS. 3-6 may also include the second electrical conductor 90 electrically connected to the active fixation device 48.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrode assembly for the positioning of an electrode of an implantable medical lead, the electrode assembly comprising:
    a housing including a proximal end for connecting to the lead and a distal end opposite the proximal end, the housing defining a housing lumen having a longitudinal axis, the housing lumen extending between the proximal end and the distal end, the housing lumen including internal screw threads extending along at least a portion of the housing lumen, and a longitudinal groove located at an outer radial surface of the housing; and
    an electrode subassembly disposed at least partially within the housing lumen, the electrode subassembly including:
        a needle electrode disposed coaxially with the longitudinal axis of the housing lumen; and
        a coupler disposed at a proximal end of the needle electrode, the coupler including external screw threads engaged with the internal screw threads of the housing lumen, wherein rotation of the coupler in a first direction moves the coupler and the needle electrode along the longitudinal axis of the housing lumen toward the distal end of the housing, and rotation of the coupler in a second direction opposite the first direction moves the coupler and the needle electrode along the longitudinal axis of the housing lumen toward the proximal end of the housing;
    an active fixation device connected to and disposed within the longitudinal groove at the outer radial surface of the housing and arranged so as to allow mapping of tissue via repositioning of the needle electrode by pushing on the lead to cause the needle electrode to penetrate the tissue and removing the needle electrode from the tissue by pulling on the lead to thereby provide mapping of the tissue prior to positioning the lead close enough to the tissue for implantation using the active fixation device.

2. The electrode assembly of claim 1, wherein when the coupler is disposed at a distal end of the portion of the housing lumen including the internal screw threads, a distal end of the needle electrode projects from the distal end of the housing and distally beyond the active fixation device.

3. The electrode assembly of claim 1, wherein the active fixation device includes a plurality of tines connected to the housing and projecting from the distal end of the housing, the tines self-biasing from a linear configuration to a curved configuration.

4. The electrode assembly of claim 1, wherein the active fixation device includes a fixation helix connected to the housing and projecting from the distal end of the housing.

5. The electrode assembly of claim 1, wherein the needle electrode includes a conical tip.

6. The electrode assembly of claim 1, wherein the housing is formed of an insulative material.

7. The electrode assembly of claim 1, wherein the coupler is rotatable by a stylet.

8. The electrode assembly of claim 1, wherein the coupler is rotatable by a coil conductor.

\* \* \* \* \*